US010080692B2

(12) United States Patent
Dold

(10) Patent No.: US 10,080,692 B2
(45) Date of Patent: Sep. 25, 2018

(54) FEMININE NEEDS CONTAINER

(76) Inventor: Elizabeth Thomas Dold, Fairfax, VA (US)

( * ) Notice: Subject to any disclaimer, the term of this patent is extended or adjusted under 35 U.S.C. 154(b) by 627 days.

(21) Appl. No.: 12/911,570

(22) Filed: Oct. 25, 2010

(65) Prior Publication Data
US 2012/0097576 A1 Apr. 26, 2012

(51) Int. Cl.
A61F 13/20 (2006.01)
A61F 13/551 (2006.01)
B65D 1/32 (2006.01)
B65D 21/08 (2006.01)

(52) U.S. Cl.
CPC .. *A61F 13/55135* (2013.01); *A61F 13/55165* (2013.01); *A61F 13/55175* (2013.01); *A61F 13/55185* (2013.01); *B65D 1/32* (2013.01); *B65D 21/086* (2013.01)

(58) Field of Classification Search
CPC .......... A61F 13/55135; A61F 13/55185; A61F 13/55175; A61F 13/55165; B65D 1/32; B65D 1/0292; B65D 21/08; B65D 21/083; B65D 21/086
USPC ................. 206/581, 577, 443, 446, 38, 235; 220/666, 530, 520, 4.28, 523, 529; 383/38–40
See application file for complete search history.

(56) References Cited

U.S. PATENT DOCUMENTS

| 1,967,859 | A | | 1/1931 | Burns | |
|---|---|---|---|---|---|
| 1,939,777 | A | * | 12/1933 | Humboldt | 215/12.1 |
| 2,026,158 | A | | 1/1934 | Bennett | |
| 2,322,920 | A | * | 6/1943 | Campbell | 206/37.3 |
| 4,201,290 | A | * | 5/1980 | Madden | 206/38 |
| 4,286,639 | A | | 9/1981 | Murphy | |
| 4,705,086 | A | * | 11/1987 | O'Neill | 150/134 |
| 4,815,510 | A | | 3/1989 | Edelist | |
| 5,244,023 | A | * | 9/1993 | Spies | 150/134 |
| 5,524,749 | A | * | 6/1996 | Thompson et al. | 206/38 |
| 5,558,214 | A | * | 9/1996 | Brundidge | 220/523 |
| 5,682,981 | A | * | 11/1997 | Sudborough | 206/38.1 |
| 5,911,338 | A | * | 6/1999 | Miller | 220/666 |
| D436,434 | S | | 1/2001 | Conway | |
| 6,289,612 | B1 | | 9/2001 | Kent | |
| 7,163,337 | B2 | * | 1/2007 | Penson | 383/38 |
| 7,866,500 | B1 | * | 1/2011 | Peggs | 220/6 |
| 2005/0109663 | A1 | | 5/2005 | Krey | |
| 2006/0237469 | A1 | * | 10/2006 | Caplicki | 220/737 |
| 2007/0241018 | A1 | | 10/2007 | Forte | |
| 2009/0069769 | A1 | | 3/2009 | Minoguchi et al. | |

(Continued)

OTHER PUBLICATIONS

"The best darn tampon holder ever!"—Tampon in lip gloss container, http://www.craftster.org/forum/index.php?topic.108216.0, downloaded Mar. 1, 2011, 6 pages.

*Primary Examiner* — Andrew Perreault

(57) ABSTRACT

A feminine needs container may comprise an elongated member having a hollow compartment, a clothing attachment member coupled to the elongated member and configured to removably attach to a garment, wherein the hollow compartment is configured to receive and store at least one feminine needs product. The elongated member can be removably attachable to the garments via the clothing attachment member such that the feminine needs container may be concealed from public view and carried hands-free without the need for a larger bag/purse to carry them.

23 Claims, 20 Drawing Sheets

(56) References Cited

U.S. PATENT DOCUMENTS

2009/0104845 A1    4/2009   Pintor et al.
2010/0051496 A1    3/2010   Watson
2010/0121299 A1    5/2010   Cooper

* cited by examiner

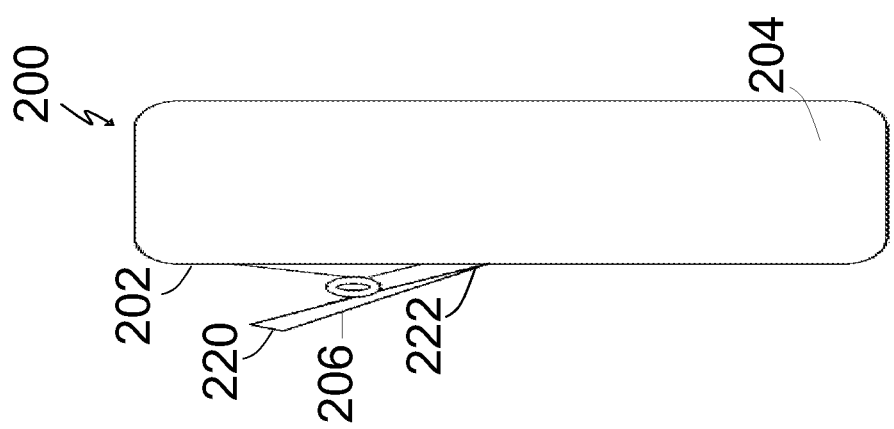

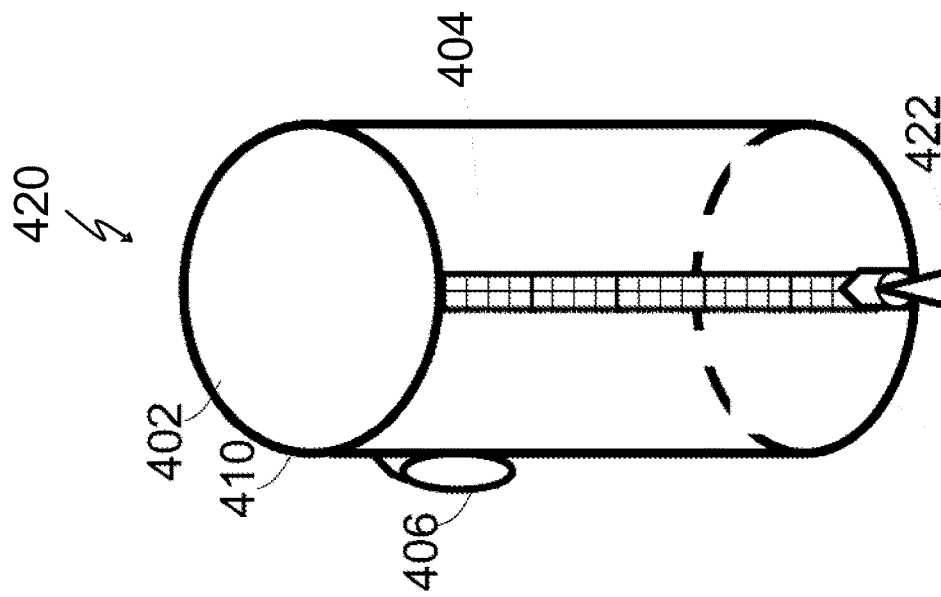
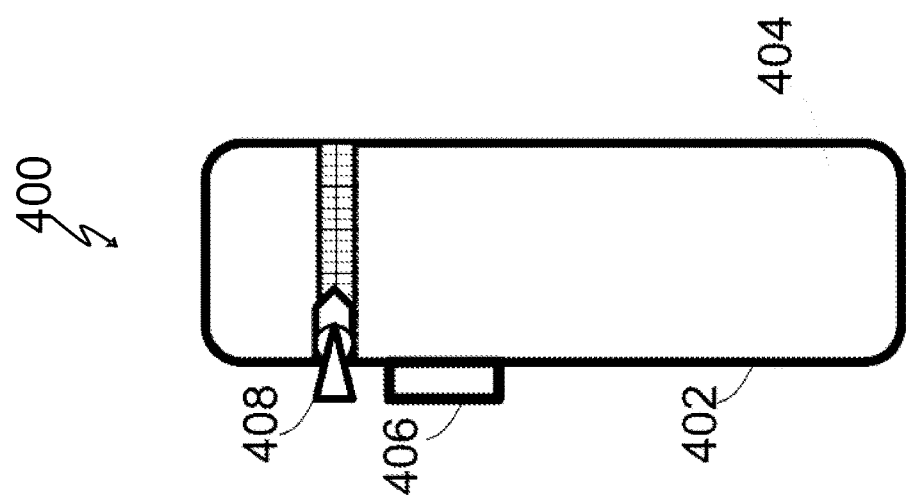

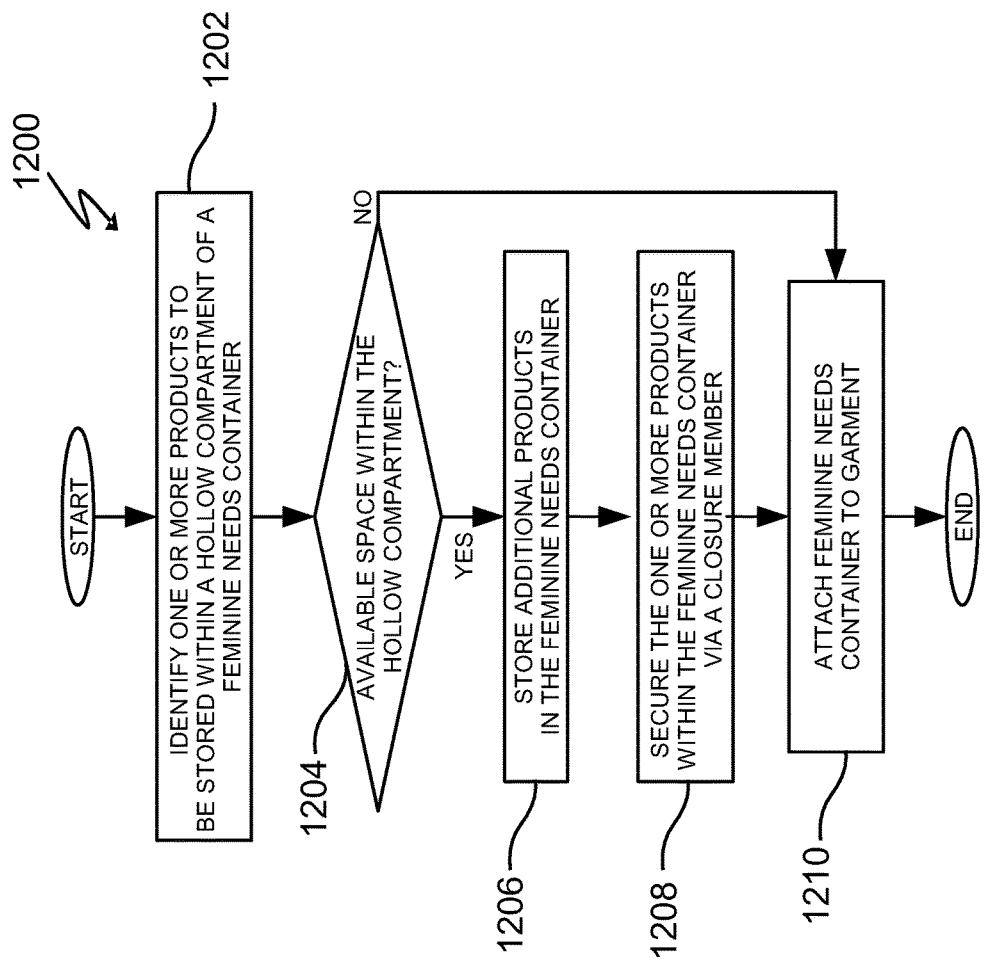

US 10,080,692 B2

FEMININE NEEDS CONTAINER

FIELD OF INVENTION

The present disclosure relates generally to a container, and more particularly, to a container to conceal feminine needs products.

BACKGROUND OF THE INVENTION

Containers offer convenient means by which to carry items and to protect the contents of the container. If containers are to be portable, they must be unobtrusive, lightweight, and appropriate for the environment in which they may be stored. The nature of the container may imply the nature of the contents. The contents may be valuable, confidential or even embarrassing, so it may be advantageous to conceal the container itself. Containers may be concealed in any number of ways such as camouflage, underneath clothing, or placed in larger containers/bags.

Women have needs related to their physiology, and they often find that dealing with physiological issues can be embarrassing. Any indication that a woman is dealing with physiological issues can be a source for public humiliation or embarrassment and is often viewed as a private matter. If a woman is attempting to deal with treating her physiological problems, she often goes to great efforts to conceal the issues. For example, women may go to great efforts to conceal their menstruation periods, along with the use of a feminine napkin or tampons while menstruating.

SUMMARY

Broadly speaking, the invention relates to a container, and more particularly, to a container used to conceal feminine needs products In one embodiment, the feminine needs container may have an elongated member having a hollow compartment, a first end, and a second end; a clothing attachment member configured to removably attach to a garment, the clothing attachment member coupled to the elongated member, wherein the hollow compartment is configured to receive and store at least one feminine needs product, and wherein the elongated member is removably attachable to a garment via the clothing attachment member such that the feminine needs container may be concealed from public view.

In another embodiment, a feminine needs container can include a compressible elongated member having a first end, a second end, and a hollow compartment, the compressible elongated member may be configured to hold at least one feminine needs product when the compressible elongated member is expanded. The feminine needs container may also have a clothing attachment member coupled to the compressible elongated member wherein the elongated member is attached to the garments via the clothing attachment member such that the feminine needs container is concealed from public view.

The above and other features will be presented in more detail in the following detailed description and the associated figures. Other aspects and advantages will become apparent from the following detailed description, taken in conjunction with the accompanying drawings.

BRIEF DESCRIPTION OF THE DRAWINGS

The accompanying drawings, which are incorporated into and constitute a part of this specification, illustrate one or more example embodiments and, together with the description of example embodiments, serve to explain the principles and implementations.

In the drawings:

FIGS. 2A and 2B illustrate side views of a feminine needs container having different embodiment of a clothing attachment member.

FIGS. 4A and 4B illustrate another embodiment of a feminine needs container.

FIG. 12 illustrates an exemplary flow diagram of a method for using the feminine needs container.

DESCRIPTION

The invention relates to a container, and more particularly, to a container used to conceal feminine needs products (including, without limitation, sanitary napkins and tampons). Unlike most containers that are carried within a larger container (e.g., backpack or purse), the container can be a mobile, hands-free container that does not require the user to carry another larger container in order to conceal the contents, and can be designed to allow for easy, safe, secure and concealed transportation of feminine needs products. This container can be carried hands-free, such as attached to the user's clothing, so that the user's clothing can effectively conceal the feminine needs products. For example, it is a convenient carrier when enjoying activities without carrying a purse/bag (e.g., school, meeting, party, club, beach, camping, boating, etc.).

Figure 1A:
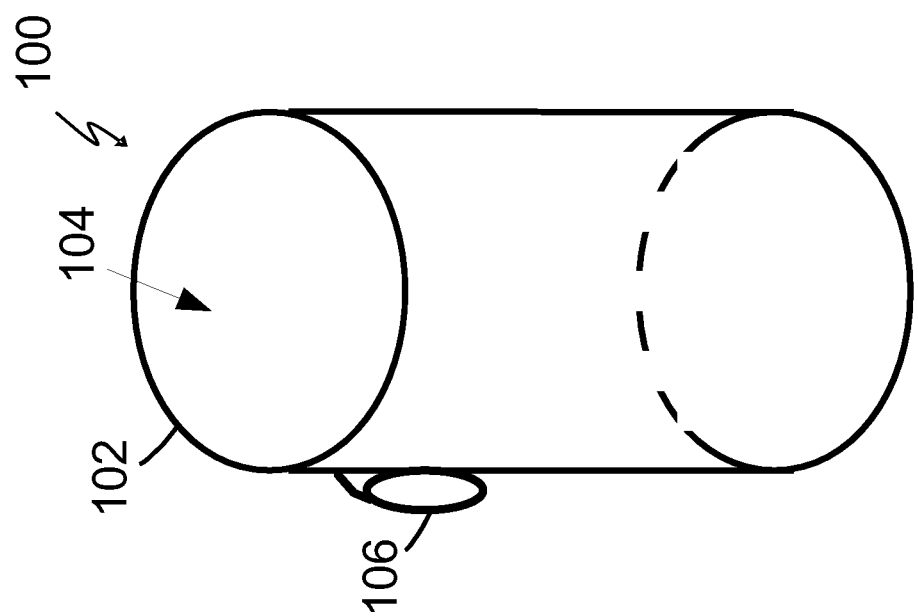
FIG. 1A illustrates a perspective view of one embodiment of a feminine needs container.
Figure 1B:
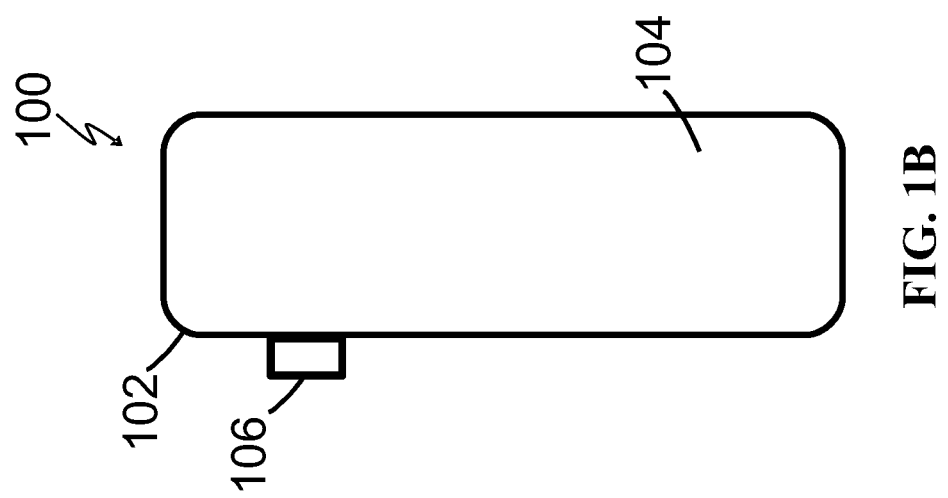
FIG. 1B illustrates a side view of the feminine needs container illustrated in FIG. 1A.

FIG. 1A illustrates a perspective view of one embodiment of a feminine needs container and FIG. 1B illustrates a side view of the feminine needs container illustrated in FIG. 1A. The feminine needs container 100 may have an elongated member 102, a hollow compartment 104, and a clothing attachment member 106. The clothing attachment member 106 can be coupled to the elongated member 102 and may be removably attached to a plurality of garments. In other words, the elongated member 102 may be attached to a plurality of garments via the clothing attachment member 106. As illustrated, the length or height and width of the clothing attachment member 106 is less than the length or height and width of the feminine needs container 100. In one embodiment, the clothing attachment member 102 may be a snap to mate with a mating snap member on a garment (not shown). In an alternative embodiment, the clothing attachment member 106 can use at least one hook and loop member (e.g., Velcro).

The hollow compartment 104 can be configured to receive and store one or more products, such as feminine products including but not limited to, birth control pills or patches (or other birth control devices), feminine napkin pads, prophylactics, sponges or towels, tampons, and the like. The feminine needs container may also be configured to receive and store other non-feminine products such as insulin shots, wet wipes, cigarette replacements, vitamins/pills, hormone supplements, and the like.

The feminine needs container 100 may be used to transport various products in a hands-free manner and may prevent embarrassment associated with the user's private needs. For example, a female, in the presence of men or other females, may need to use or change a tampon during menstruation. It may be embarrassing for the woman to take her purse with her to the bathroom as the men may assume, correctly so, that she is menstruating. The feminine needs container 100 may be used to conceal the tampon underneath at least one of her plurality of garment. In doing so, the female can avoid embarrassment, shame, and insecurity or otherwise disclosure of her current physiological issues. By attaching the feminine needs container 100 under one of a plurality of garments, the feminine needs container 100 can be concealed thereby preventing any embarrassment, shame or detection for the user when carrying and/or using the feminine needs products.

The elongated member 102 may store the feminine needs products in the hollow compartment 104 of the elongated member. The elongated member 102 may be made from any known material. For example, the material may be pliable, flexible, malleable, rigid, or any combination thereof. The material may be any known material such as metal, plastic, fabric, wood, a combination thereof, and the like. The material may disposable to facilitate a one-time use and may be waterproof and lightweight. In one embodiment, the elongated member may contact the skin of the user and thus should be made with a soft malleable material that is comfortable for the user.

The clothing attachment member 106 may be coupled to the elongated member 102. The clothing attachment member 106 may be coupled to any portion of the elongated member 102. The clothing attachment member 106 may be attached to the elongated member by any means including, but not limited to, adhesive, clips, snaps, hook and loop fasteners (e.g., Velcro), clamps, any combination thereof, and the like. The clothing attachment member 106 may be designed to be removably attached to a garment to conceal the feminine needs container 100 from public view. The clothing attachment member 106 may be any attachment device capable of attaching to an article of clothing, such as, but not limited to, a clothespin, a clip, button, snap, a drawstring, a pin, a hook and loop fastener, or any other known device. In the event that the user is wearing a garment that does not have a suitable means to attach the clothing attachment, in one embodiment a body belt (which can be made of any known material (e.g., fabric with clothing attachment member) can be used to attach the clothing attachment to; this is similar to a garter or belt (that varies is length) that can be worn against the body to support the clothing attachment (e.g., secured about the waist, thigh or chest).

Figure 2B:
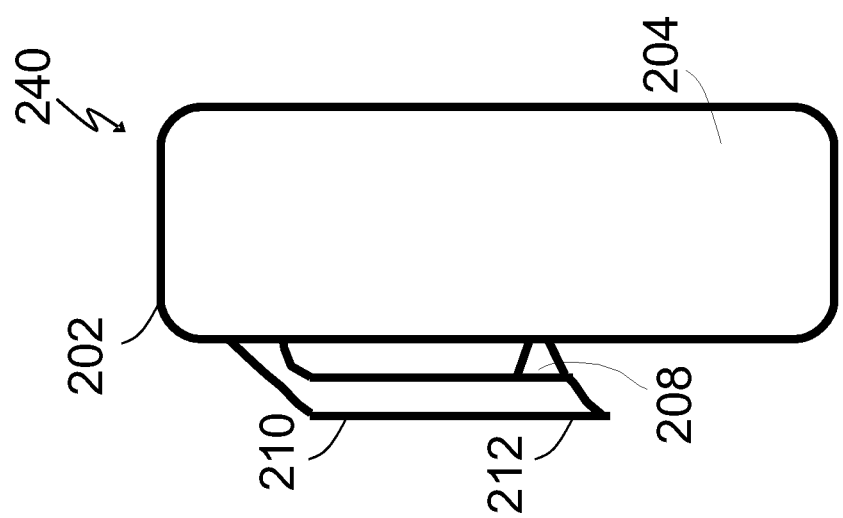

FIGS. 2A and 2B illustrate side views of a feminine needs container having different embodiment of a clothing attachment member. FIG. 2A illustrates a clasp 206 attached to the elongated member 202. Referring to FIG. 2A, the clasp 206 may be configured to apply pressure between the garment and the elongated member 202 to attach the feminine needs container 200 to the garment. In use, the user may apply pressure to the top portion 220 of the clasp 206, which releases the bottom portion 222 of the clasp 206 from the elongated member 202. A garment may be positioned in the opening between the bottom portion 222 of the clasp 206 and the elongated member 202. The user may release the top portion 220 of the clasp 206, whereby the pressure between the bottom portion 222 and the elongated member 202 secures the feminine needs container 200 to the garment.

Referring to FIG. 2B, the clip 210 attached to the elongated member 202 may be used to attach the feminine needs container 240 to a plurality of garments. A distal end 212 of the clip 210 may have a protruding member 208 that protrudes medially towards the feminine needs container 240. A portion of garment can be slipped between the clip 210 and the elongated member 202. The protruding member 208 may apply pressure to the garment against the elongated member 202 in order to secure the garment. The clip 210 may be attached to the elongated member by any attachable means including, but not limited to, adhesive, staples, nails, screws, bolts, welding, molded onto the elongated member 202, and the like.

Figure 3B:
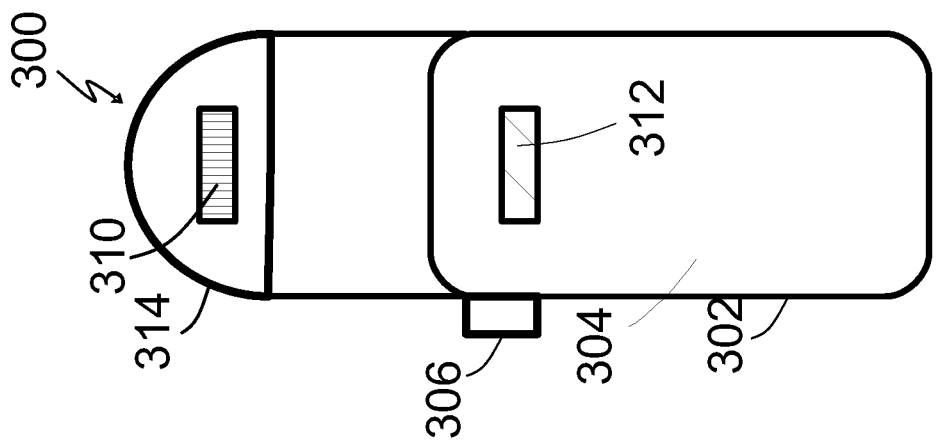
FIG. 3A and FIG. 3B illustrate side views of an alternative embodiment of a feminine needs container.
Figure 3A:
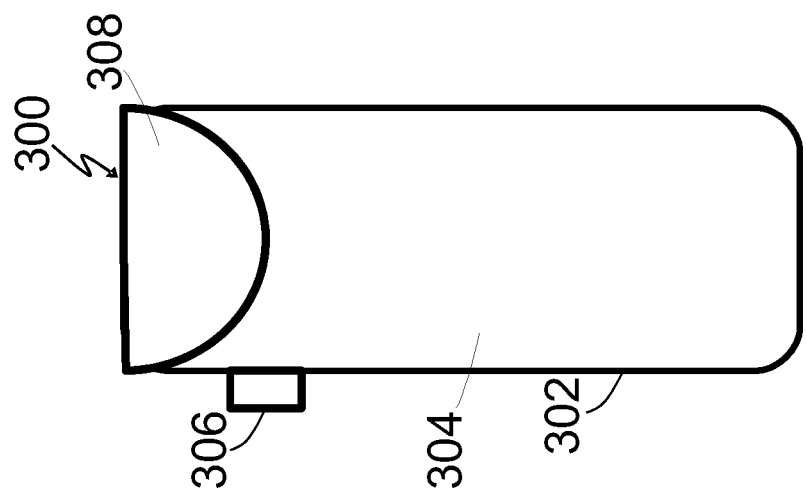
Figure 5B:
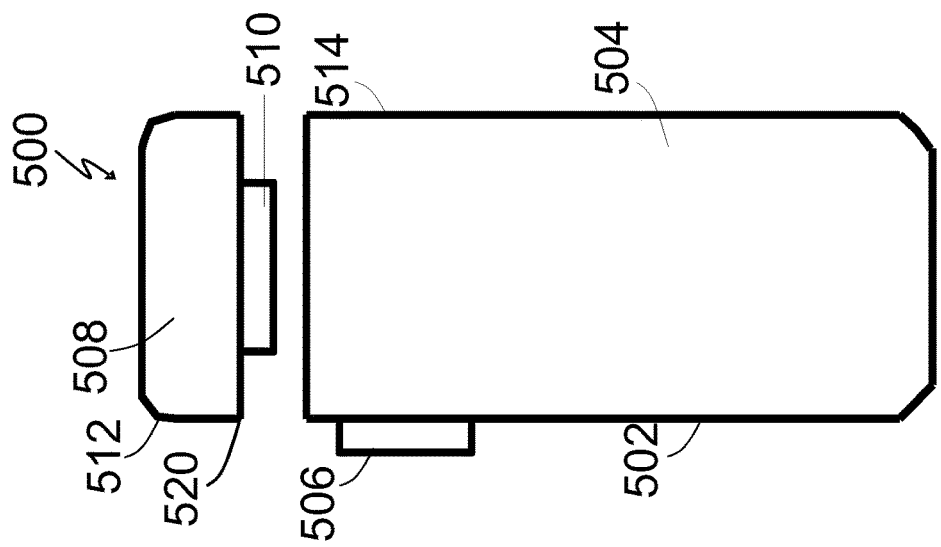
FIGS. 5A and 5B illustrate side views of a feminine needs container having another embodiment of a clothing attachment member.
Figure 5A:
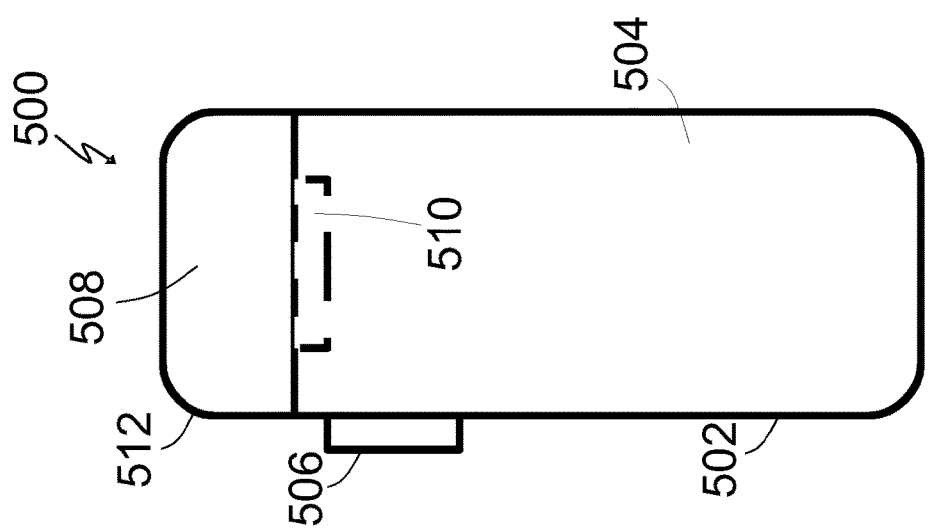

FIG. 3A and FIG. 3B illustrate side views of an alternative embodiment of a feminine needs container FIG. 3A illustrates a closure member 308 in a closed position and FIG. 3B illustrates the closure member 308 in an open position. The feminine needs container 300 may comprise an elongated member 302, a hollow compartment 304, and a clothing attachment member 306 similar to the elongated member 102, hollow compartment 104, and clothing attachment member 106 of FIGS. 1A and 1B. The feminine needs container may also have a closure member 308. The closure member 308 may be any means or device to substantially close the feminine needs container 300 and secure a plurality of contents therein, such as a hook and loop fastener 310, 312 (as illustrated in FIGS. 3A and 3B), a zipper (as illustrated in FIGS. 4A and 4B), a seal and cap device (as illustrated in FIGS. 5A and 5B), and any other closure mean or device. The closure member 308 may be used to hide the plurality of contents within the hollow compartment 304 and/or prevent the plurality of contents from falling out of the feminine needs container 300.

In one embodiment, the closure member 308 may have a flap 314 designed to extend beyond a length of the elongated member 308. The flap 314 may be formed as a part of the elongated member 302 or may be a separate device attached to the elongated member 302. The flap 314 may be made of any pliable or flexible material including, but not limited to, rubber, fabric, plastic, metal, or the like. The closure member 308 may include a hook portion 310 and a loop portion 312. The closure member 308 may be transitioned from the open position (illustrated in FIG. 3A) to the closed position (illustrated in FIG. 3B) by mating the hook portion 310 with the loop portion 312. The closure member 308 may be changed from the closed to the open position by uncoupling the hook portion 310 from the loop portion 312 and lifting flap 314. Flap 314 can close off the feminine needs container 300 to conceal the products within the hollow compartment 304. The hook portion 310 and loop portion 312 may be located on any portion of the feminine needs container 300 as long as it secures the closure member 308. The hook and loop fastener 310, 312 can provide an easy way to expose the products secured within the feminine needs container 300 as well as to prevent the products from falling out of the feminine needs container 300. In another embodiment, the hook and loop fastener may be positioned on the feminine needs container 300 and the garment. For example, a hook portion may be positioned on the feminine needs container 300 to be coupled with a fastener portion on the garment.

FIGS. 4A and 4B illustrate another embodiment of a feminine needs container. FIG. 4A illustrates a side view of one embodiment the feminine needs container having a horizontal closer member. The feminine needs container 400 may have an elongated member 402 having a first end 410 and a second end 412, a hollow compartment 404, and a clothing attachment member 406, similar to the elongated member 102, hollow compartment 104, and clothing attachment member 106 of FIGS. 1A and 1B. The feminine needs container 400 may also have a closure member 408. As illustrated, the closure member 408 may be a zipper positioned horizontally, or parallel to the first end 410 and the second end 412. In use, the zipper can conceal products within the feminine needs container 400 when in a closed position. The zipper can expose the products within the feminine needs container 400 when in an open position.

FIG. 4B illustrates yet another embodiment of a feminine needs container 420 having a vertical closure member 422. As illustrated, the closure member 422 may be a zipper positioned to run from the first end 410 to the second end 412 of the elongated member 402. In use, products within the hollow compartment 404 may be exposed with the zipper is positioned in an opened position. Products within the hollow compartment 404 may be concealed or stored within the hollow compartment 404 when the zipper is positioned in a closed position.

FIGS. 5A and 5B illustrate side views of a feminine needs container having another embodiment of a clothing attachment member. The feminine needs container 500 may have an elongated member 502, a hollow compartment 504, and a clothing attachment member 506, similar to the elongated member 102, hollow compartment 104, and clothing attachment member 106 of FIGS. 1A and 1B. The feminine needs container may also have a closure member 508 having a cap member 512 and a seal member 510. FIG. 5A illustrates the feminine needs container 500 with the closure member 508 in a closed position to conceal the hollow compartment 504. FIG. 5B illustrates the feminine container 500 with the closure member 508 in an open position to expose the hollow compartment 504. Referring to FIG. 5A, the closure member 508 may be positioned at a top end 514 of the feminine needs container 500 to secure a plurality of products within the hollow compartment 504. The hollow compartment 504 may receive the seal member 510 when the closure member 508 is in the closed position. As illustrated in FIG. 5B, the closure member 508 may be removed from the top end 514 to expose the products stored within the hollow compartment 504. The seal member 510 may be coupled to a bottom surface 520 of the closure member 508 by any known attachment means such as the use of adhesives, bolts, screws, and the like. In another embodiment, the cap member 512 and the seal member 510 may be molded as a single piece.

Figure 6:
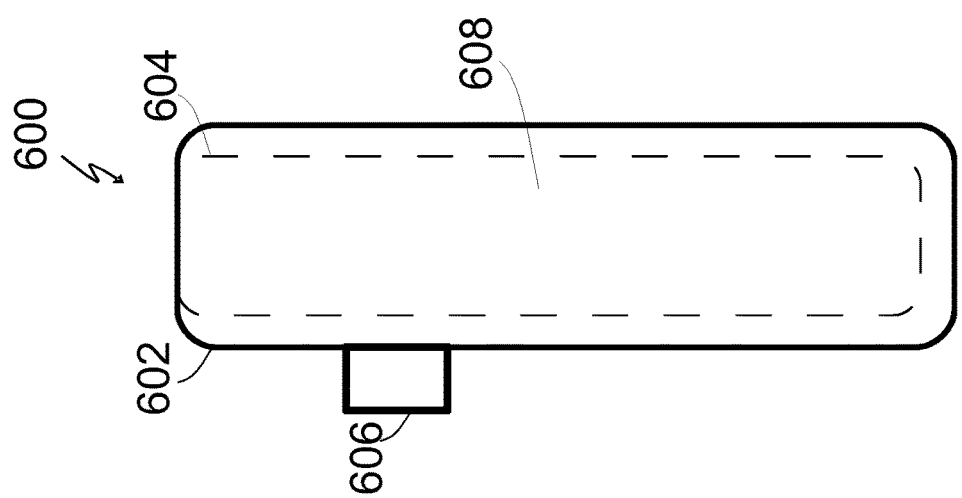
FIG. 6 illustrates a side view of a feminine needs container storing a product.

FIG. 6 illustrates a side view of a feminine needs container storing a product. The feminine needs container 600 comprises an elongated member 602, a hollow compartment 604, and a clothing attachment member 606 similar to the elongated member 102, hollow compartment 104, and clothing attachment member 106 of FIGS. 1A and 1B. The product 608 can be stored in the hollow compartment 604 concealed from public view. In one embodiment, the product 608 may be an embarrassing feminine item, including but not limited to, birth control pills or patches, feminine napkins, prophylactics, sponges, douche, tampons, and the like. In another embodiment, the product 608 may be any item such as insulin or hormone shots, wet wipes, tissues, or the like.

Figure 7A:
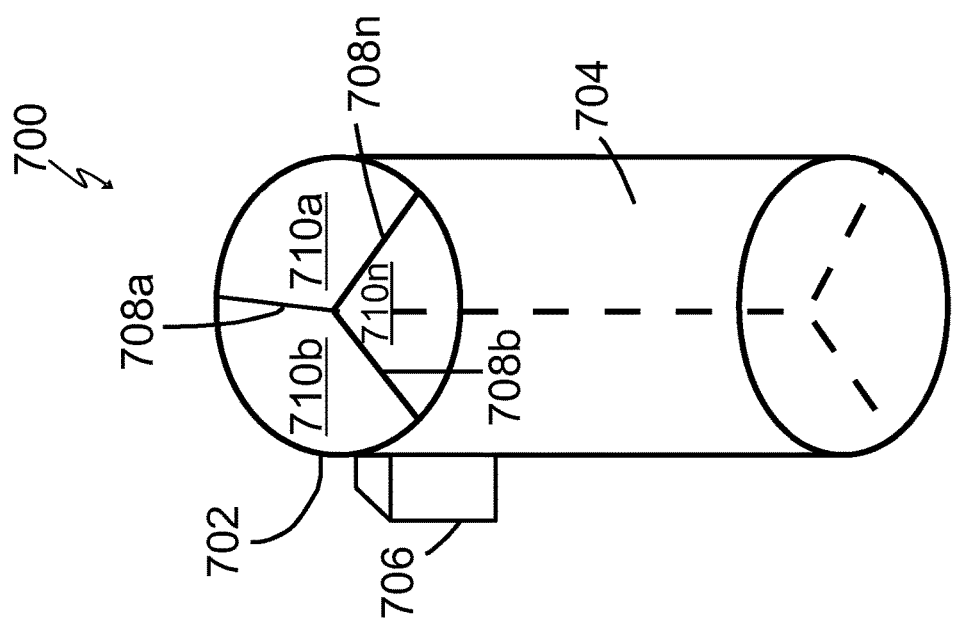
FIGS. 7A and 7B illustrate perspective views of one embodiment of a feminine needs container having multiple compartments.
Figure 7B:
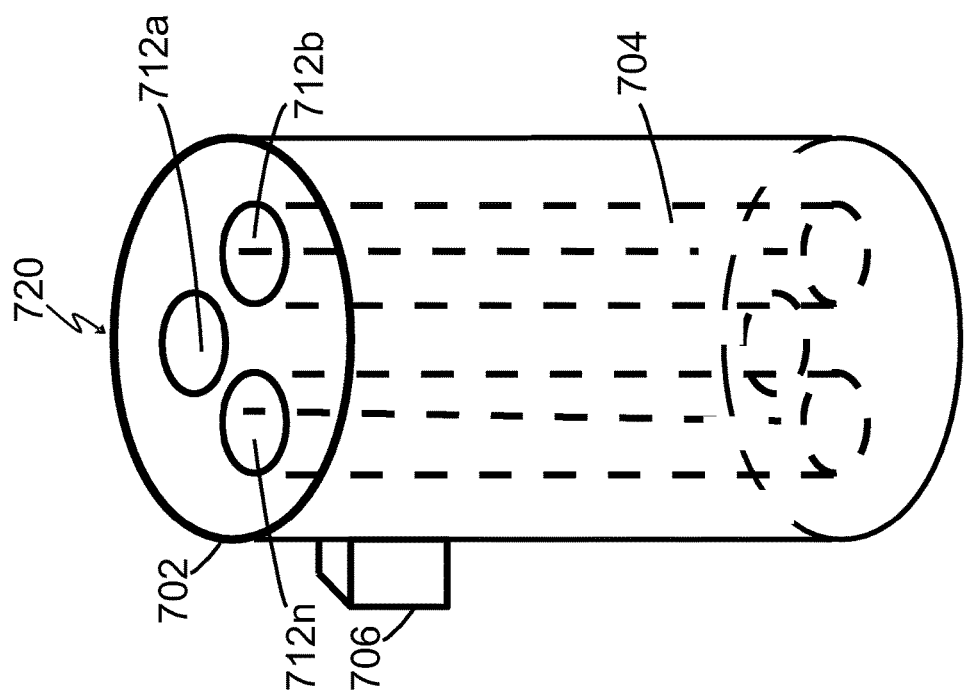

FIGS. 7A and 7B illustrate perspective views of one embodiment of a feminine needs container having multiple compartments. The feminine needs container 700 may have an elongated member 702, a hollow compartment 704, and a clothing attachment member 706 similar to the elongated member 102, hollow compartment 704, and clothing attachment member 106 of FIGS. 1A and 1B. The feminine needs container 700 may also have and a plurality of division slats 708a, 708b, 708n (where n is an integer) positioned within the hollow compartment 704. The division slats 708a-n may form a plurality of storage compartments 710a, 710b, 710n within the hollow compartment 704. Although illustrated with three storage compartments, this number is not meant to be limiting as any number of division slats 708a-n may be used to form any number of storage compartments.

Having multiple storage compartments 710a-n allow a user to store multiple items within the feminine needs container 700. Furthermore, multiple storage compartments 710a-n may be used for products that may need to be separated. For example, if one of the products needs to be kept in a cool environment, one of the storage compartments may be used to store a cold gel pack or any other cooling device.

Referring to FIG. 7B, in another embodiment, the feminine needs container 720 may have a plurality of chambers 712a, 712b, 712n. Although illustrated with three chambers 712a-n, this number is not meant to be limiting as any number of chambers may be used to form any number of storage compartments. Having multiple chambers 712a-n allow a user to store multiple items within the feminine needs container 720. Furthermore, multiple chambers 712a-n may be used for products that may need to be separated. For example, if one of the products needs to be kept in a cool environment, one of the storage compartments may be used to store a cold gel pack or any other cooling device.

Figure 8:
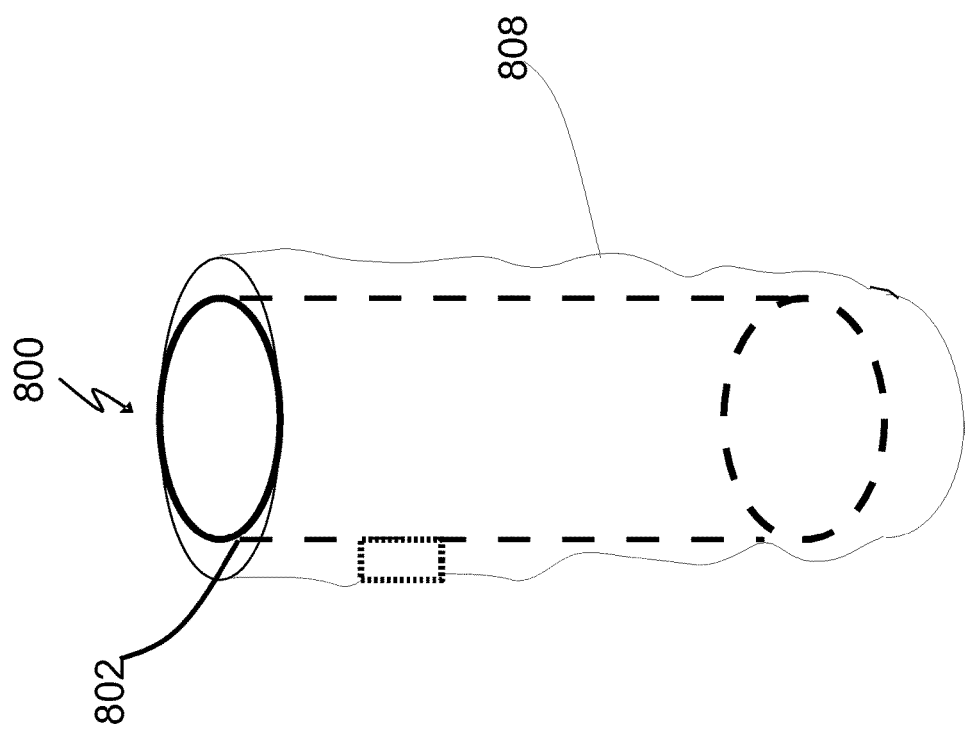
FIG. 8 illustrates a perspective view of another embodiment of a feminine needs container.

FIG. 8 illustrates a perspective view of another embodiment of a feminine needs container. The feminine needs container 800 may have a sheath 808 positioned around the outer perimeter of the elongated member 802 The sheath 808 may be formed of a waterproof material to prevent moisture (or water) from entering the feminine needs container 800. The sheath 808 may also be a soft material to make the feminine needs container 800 more comfortable when positioned against the skin of the user.

Figure 9:
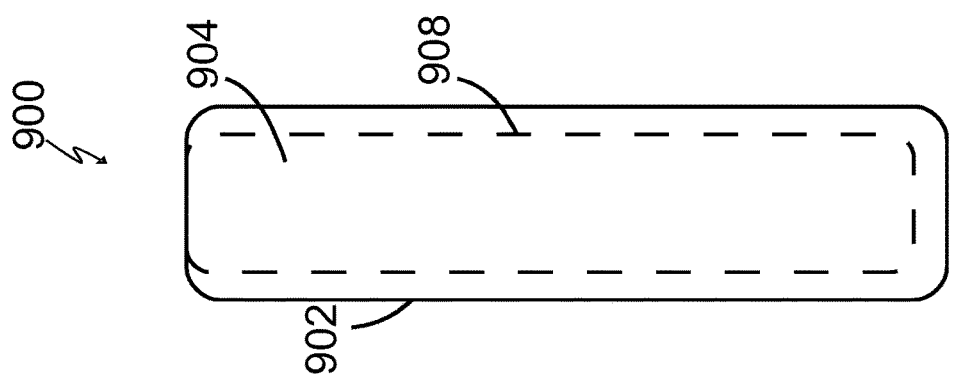
FIG. 9 illustrates a side view of yet another embodiment of a feminine needs container.

FIG. 9 illustrates a side view of yet another embodiment of a feminine needs container. The feminine needs container 900 may have an interior liner 908 disposed within the hollow compartment 904. In other words, the interior liner 908 may be coupled to the interior perimeter of the elongated member 902. The interior liner 908 may make insertion of a product into the hollow compartment 904 easier for a user. The interior liner 908 may also function as a cushion to reduce damage to the product stored within the hollow compartment 904.

Figure 10:
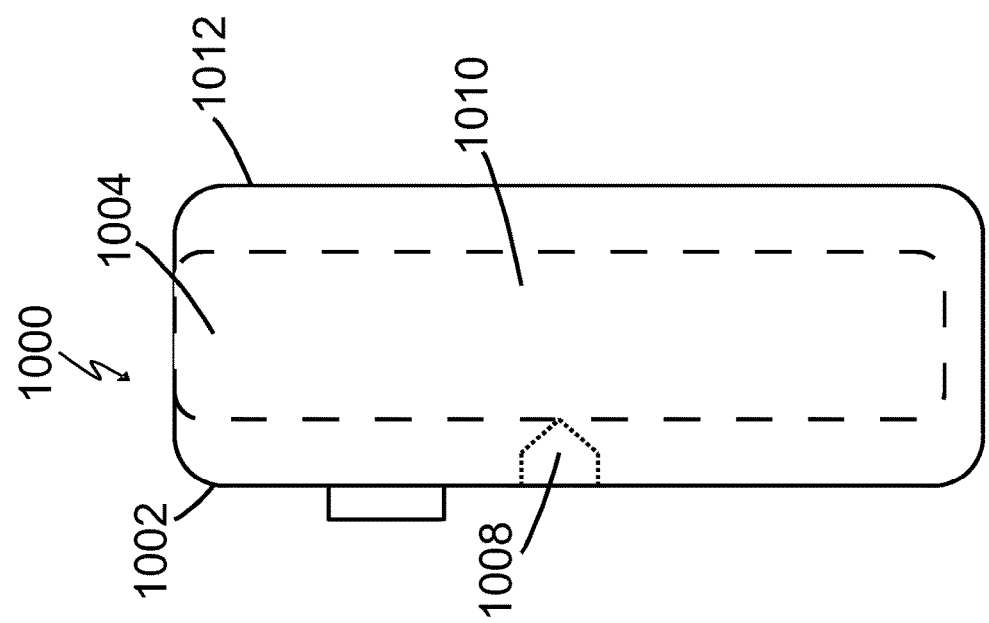
FIG. 10 illustrates a side view of still another embodiment of a feminine needs container.

FIG. 10 illustrates a side view of still another embodiment of a feminine needs container. The feminine needs container 1000 may have a pressure fit member 1008 coupled to the interior surface of the elongated member 1002. The pressure fit member 1008 may be designed to secure at least one product 1010 within the hollow compartment 1004. In one embodiment, the feminine needs container 1000 may have an opening at a top end 1012. Thus, the pressure fit member 1008 may be used to secure the at least one product 1010 within the hollow compartment 1004 and prevent the at least one product 1010 from falling out of the feminine needs container 1000. In use, the pressure fit member 1008 may exert pressure onto the product 1010 such that the product is secured by the pressure against the interior of the elongated member 1002. Having a feminine needs container 1000 with an opening at a top end 1012 may facilitate convenient, quick and easy access to the product 1010.

Figure 11B:
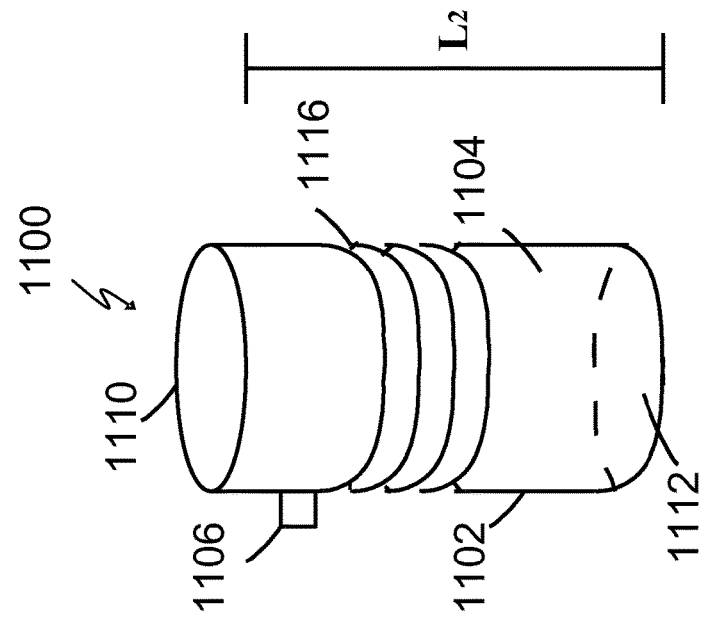
FIGS. 11A and 11B illustrate perspective views of yet another embodiment of a feminine needs container.
Figure 11A:
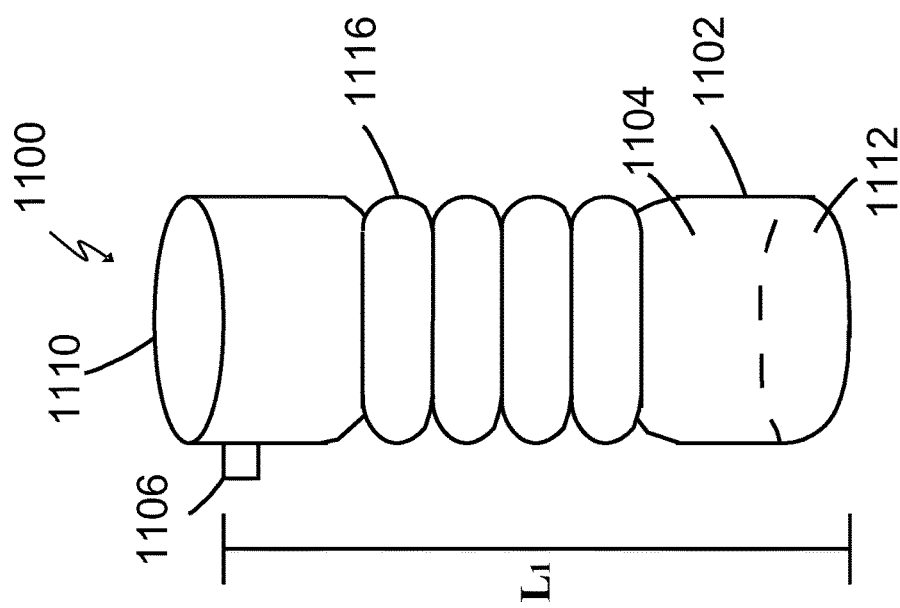

FIGS. 11A and 11B illustrate perspective views of yet another embodiment of a feminine needs container. The feminine needs container 1100 may have an elongated member 1102, a hollow compartment 1104, and a clothing attachment member 1106. The elongated member 1102 may have a top section 1110, a bottom section 1112, and a compressible section 1116.

In one embodiment, as illustrated, the compressible section 1116 can be positioned between the first end 1110 and the second end 1112 of the elongated member 1102. The compressible section 1116 of the elongated member 1102 may be comprised of any rigid malleable material capable of being compressed and uncompressed. By way of example, the compressible section 1116 may be formed from a malleable, yet rigid, plastic. In another embodiment, the compressible section 1116 may be formed of rubber, metal, any combination thereof, or any other similar material. The compressible section 1116 may be coupled to the first end 1110 and the second end 1112 by any means. For example, the compressible section 1116 may be coupled to the first end 1110 and the second end 1112 by welding, adhesives, sewing, or the like.

The compressible section 1116 may allow a user to insert products of different lengths. Referring to FIG. 11A, the compressible section 1116 is illustrated in an uncompressed state. The uncompressed state may be considered an "extended" state. The length of the elongated member 1102 may be at its maximum length, $L_1$, because the compressible section 1116 is in its "extended" position. At its maximum length, the elongated member 1102 may be configured to receive products of various lengths.

Referring to FIG. 11B, the compressible section 1116 is illustrated in a compressed state. In this position, the elongated member 1102 may be at its minimum length $L_2$. In use, the length of the elongated member 1102 may be adjusted by either compressing or uncompressing the compressible section 1116. This allows for the storage of products having varying lengths such that the top section 1110 and the bottom section 1112 of the elongated member 1102 are relatively adjacent to the ends of the product. For example, if the product has a length less than $L_1$, the user may compress the compressible section 1116 to the length of the product. This provides for a feminine needs container that is compact and may be more portable to carry on a user's garment and concealed from public view. In one embodiment, the compressible section 1116 can be returned to a compressed state when no longer holding a product.

FIG. 12 illustrates an exemplary flow diagram of a method for using the feminine needs container. A user may identify one or more products to be stored within a hollow compartment of a feminine needs container at 1202. The feminine needs container may have an elongated member, a hollow compartment, and a clothing attachment member as discussed above. The clothing attachment member can be coupled to the elongated member and can be removably attached to garments. The hollow compartment can be configured to receive and store one or more products such as birth control pills or patches, feminine napkins, prophylactics, sponges, douche, tampons, and the like. In another embodiment, the one or more products may be any item such as insulin shots, wet wipes, tissue, or the like. The feminine needs container may be a way to transport products to prevent embarrassment, shame, or insecurity to the user or to prevent disclosure. For example, a female in a presence of others may need to use or change a tampon during menstruation. The woman may be too ashamed, self conscious, or embarrassed to take her purse or bag with her to the restroom because others may assume or realize she is menstruating, which may be an embarrassment to the female. Alternatively, the women may not want to carry a purse/bag (or other container to conceal the products) with her person as the purse/bag may be inappropriate/undesired/impermissible for the event. Thus, the female may use the feminine needs container to conceal the tampon underneath her garments. In doing so, the woman can avoid the embarrassment of carrying the purse to the bathroom. By allowing the feminine needs container to be attached to an undergarment, the feminine needs container can be concealed and thereby can prevent any embarrassment, shame or disclosure for the user when carrying and/or using the feminine needs products.

The elongated member may be formed of any known material such as any pliable, flexible, malleable, rigid, soft, waterproof, any combination thereof, and the like. The material may be any known material such as, but is not limited to metal, plastic, fabric, wood, any combination thereof, and the like. The color of the elongated member can be chosen to match the user's skin tone, can be chosen to match the color of the garment, or can simply be chosen in view of the user's individual design choice.

The feminine needs container may also have the clothing attachment member coupled to the elongated member. The clothing attachment member may be coupled to any portion of the elongated member. The clothing attachment member may be attached to the elongated member by any means including, but not limited to the use of adhesives, clips, hook and loop fasteners, snaps, clamps, any combination thereof, or the like. The clothing attachment member may be designed to be removably attached to a garment to conceal the feminine needs container from public view. The clothing attachment member may be any attachment device capable of attaching the feminine needs container to an article of clothing, such as, but not limited to, a clothespin, clip, snap, drawstring, pin, hook and loop fastener, or any other known means to detachably couple the feminine needs container to a garment.

A determination may then be made as to whether there is available space within the hollow compartment at 1204 to store the one or more feminine needs products. The hollow compartment may be of sufficient size to store at least one product; however additional products may be stored in the feminine needs container if additional space is available.

When it is determined that no additional space is available at 1204, the feminine needs container may be attached to the user's garment at 1208 via the clothing attachment member. If it is determined that there is sufficient space available to store the additional products at 1206, the user may store additional products in the feminine needs container at 1206. The feminine needs container may be attached to the user's garment at 1208 using the clothing attachment member. Prior to attachment to the user's garment at 1208, a closure member may secure the feminine needs product within the feminine needs container at 1210. The closure member may be any means or device to substantially close the feminine needs container and secure the contents therein, including, but not limited to a hook and loop fastener (as illustrated in FIGS. 3A and 3B), a zipper (as illustrated in FIGS. 4A and 4B), a seal and cap device (as illustrated in FIGS. 5A and 5B), or any other closure devices.

Figure 13B:
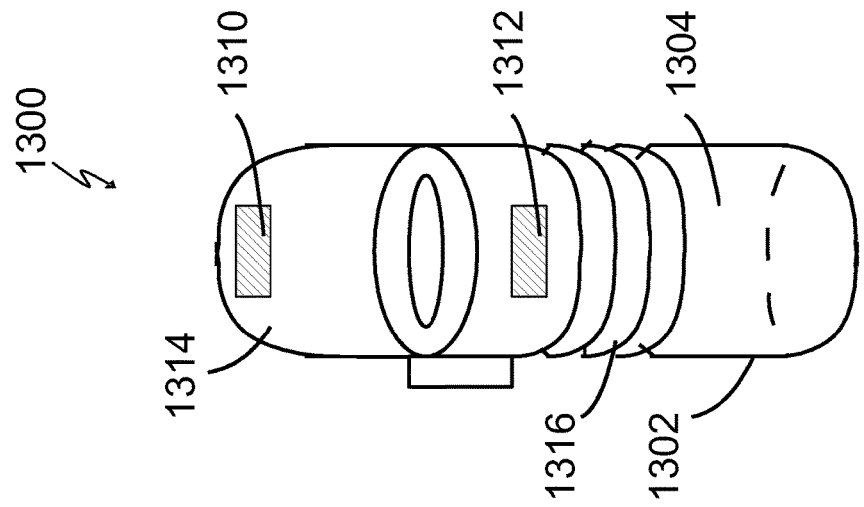
FIGS. 13A and 13B illustrate perspective views of another embodiment of a feminine needs container.
Figure 13A:
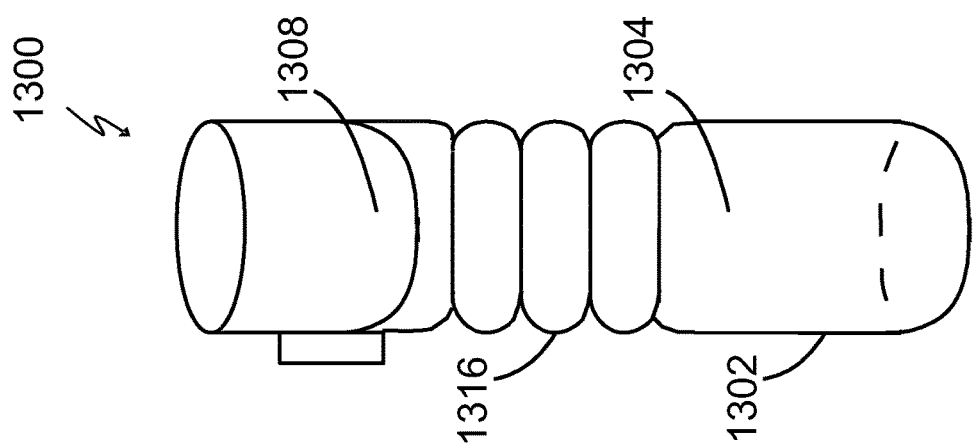

FIGS. 13A and 13B illustrate perspective views of another embodiment of a feminine needs container. The feminine needs container 1300 is similar to the feminine needs container illustrated in FIGS. 11A and 11B. However, the feminine needs container 1300 may also include a closure member 1308 similar to the closure member discussed and illustrated in FIGS. 3A and 3B.

Referring to FIG. 13A, the compressible section 1316 may be in an uncompressed "extended" state. The length of the elongated member 1302 may be considered at its maximum length because the compressible section 1316 is "extended" to its maximum length or position. The feminine needs container 1300 is also illustrated with the closure member 1308 in a closed position to seal the products within the hollow compartment 1304 of the elongated member 1302.

FIG. 13B illustrates the compressible section 1316 in a compressed state and the closure member 1308 in an open position. In this position, the elongated member 1302 may be at its minimum length. In use, the length of the elongated member 1302 may be adjusted by either compressing or uncompressing the compressible section 1316. This allows for the storage of products having varying lengths.

Figure 14:
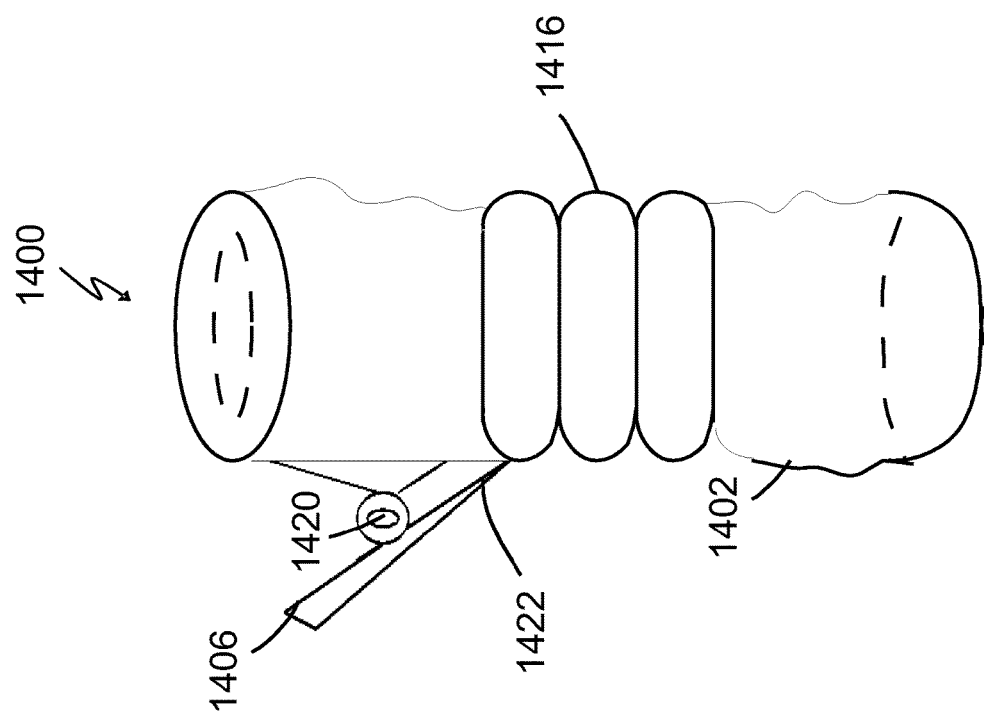
FIG. 14 illustrates a perspective view of a feminine needs container having another embodiment of a clothing attachment member.

FIG. 14 illustrates a perspective view of a feminine needs container having another embodiment of a clothing attachment member The feminine needs container 1400 is similar to the feminine needs container illustrated in FIGS. 11A and 11B having a compressible section 1416. The feminine needs container 1400 includes a clothing attachment member similar to the clothing attachment member illustrated in FIG. 2A. The clothing attachment member may be a clasp 1406 configured to apply pressure between the garment and the elongated member 1402 to attach the feminine needs container 1400 to the garments. In use, the user may apply pressure to the top portion 1420 of the clasp 1406, which releases the bottom portion 1422 of the clasp 1406 from the elongated member 1402. A garment may be positioned in the opening between the bottom portion 1422 of the clasp 1406 and the elongated member 1402. The user may release the top portion 1420 of the clasp 1406, whereby the pressure between the bottom portion 1422 and the elongated member 1402 secures the feminine needs container 1400 to the garment.

Figure 15:
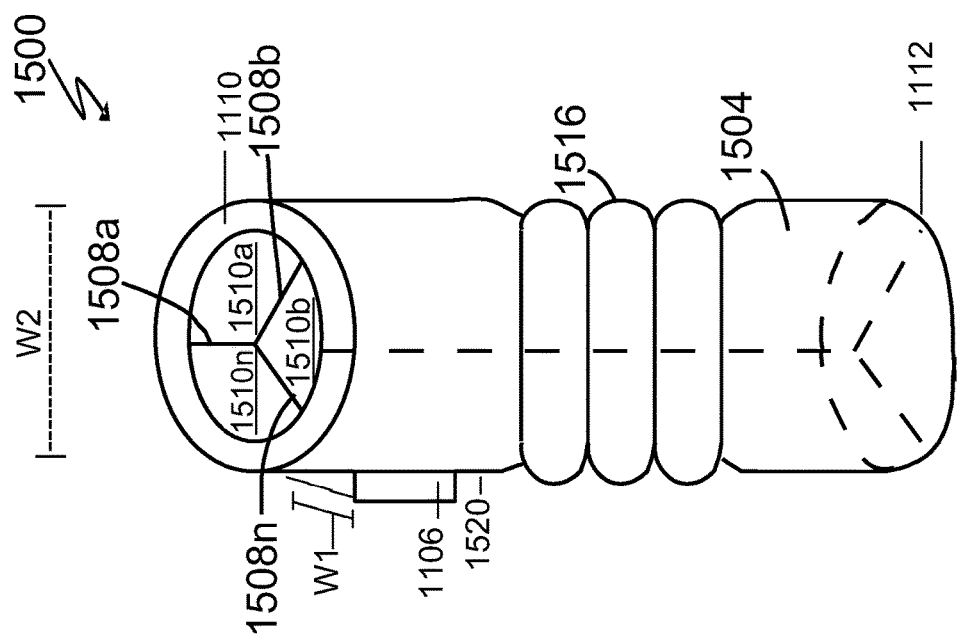
FIG. 15 illustrates a perspective view of one embodiment of a hollow compartment of the feminine needs container.

FIG. 15 illustrates a perspective view of one embodiment of a hollow compartment of the feminine needs container. The feminine needs container 1500 may be similar to the feminine needs container illustrated in FIG. 11A having a compressible section 1516. The clothing attachment member 1106 may be coupled to a side 1520 of the feminine needs container 1500. The feminine needs container 1500 may have a width W2 that is greater than the width W1 of the clothing attachment member 1106. The feminine needs container 1500 may also have a plurality of division slats 1508a, 1508b, 1508n positioned within the hollow compartment 1504. The division slats 1508a-n may form a plurality of storage compartments 1510a, 1510b, 1510n within the hollow compartment 1504. Although illustrated with three storage compartments, this number is not meant to be limiting as any number of division slats 1508a-n may be used to form any number of storage compartments.

Having multiple storage compartments 1510a-n allow a user to store multiple items within the feminine needs container 1500. Furthermore, multiple storage compartments 1510a-n may be used for products that may need to be separated. For example, if one of the products needs to be kept in a cool environment, one of the storage compartments may be used to store a cold gel pack or any other cooling device.

Figure 16:
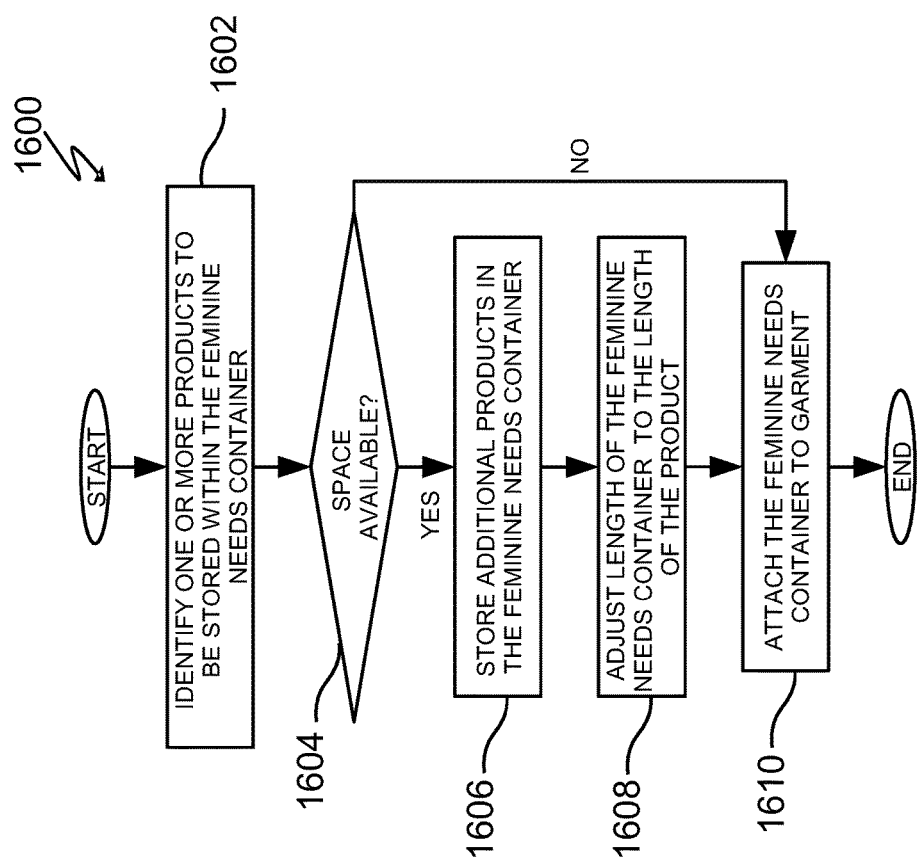
FIG. 16 illustrates a flow diagram of a method for using a feminine needs container.

FIG. 16 illustrates a flow diagram of a method for using a feminine needs container. The method for using a feminine needs container 1600 may provide for the identification of one or more products to be stored within the feminine needs container at 1602. The feminine needs container may be any of the feminine needs containers discussed above, for example, in FIGS. 1A, 2A, 2B, 3A, 3B, 4A, 4B, 5A, and 5B.

A determination is made as to whether there is available space at 1604 within the hollow compartment of the feminine needs container to store additional products. The hollow compartment may have sufficient area, space, or size to store one product; however additional products may be stored in the feminine needs container if additional space is available.

When it is determined that no available space is available at 1604, the feminine needs container may be attached to the user's garment at 1610. When it is determined that there is available space at 1604, the additional products may be stored in the feminine needs container at 1606. The length of the feminine needs container may be adjusted to the lengths of the products at 1608. The feminine needs container may have a compressible section that may be in a compressed state or an uncompressed state. In use, the length of the feminine needs container may be adjusted by either compressing or uncompressing the compressible section. This allows for the storage of products having varying lengths and provides for a feminine needs container that is compact and may be more portable to carry on a user's garment where it is concealed from public view.

If the feminine needs container has a closure member, such as the closure member discussed in FIGS. 3A, 3B, 4A, 4B, and 5A and 5B, the feminine needs container may be secured using the closure member. The feminine needs container may be attached to the user's garment at 1610. Once the contents of the feminine needs container is used or otherwise disposed of, the feminine needs container may be collapsed or compressed further via the compressible section. In one embodiment, the collapsed feminine needs container may have a height of between 1-2 inches. In another embodiment, the collapsed feminine needs container may have a height of less than 1 inch. This provides for a compact feminine needs container that, for example, can allow the user to easily put the feminine needs container in her pocket to be thrown away or disposed of and/or reused at a later time.

Figure 17:
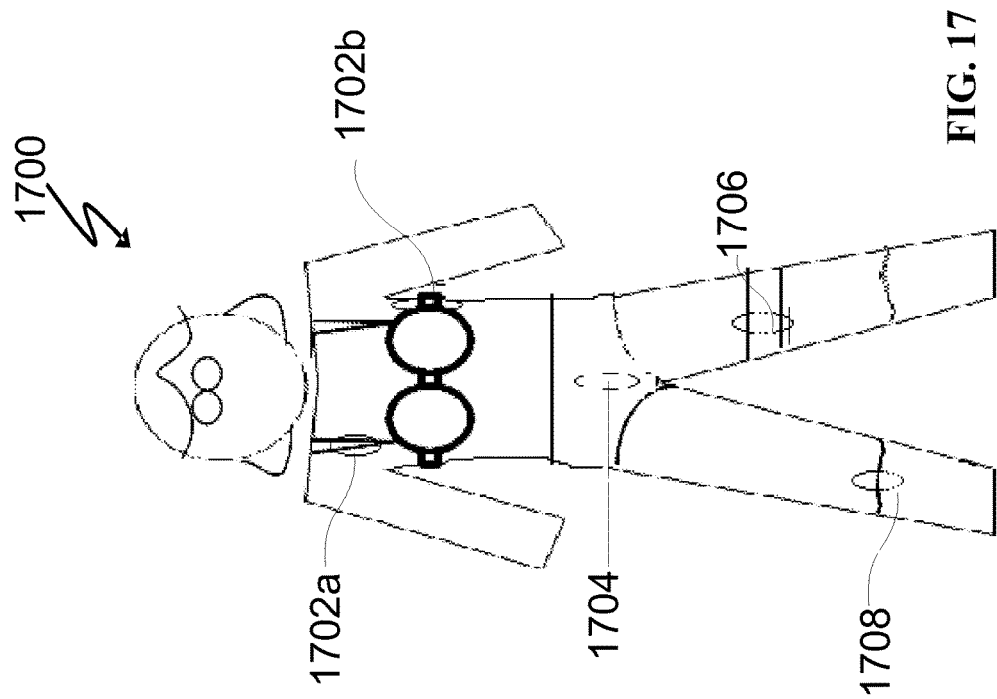
FIG. 17 illustrates placements of the feminine needs container on various garments.

FIG. 17 illustrates placements of the feminine needs container on various garments. In one example, the feminine needs container 1700 may be removably attached to the user's under garments such as bra straps 1702a, 1702b or underwear 1704. In other example, the feminine needs container 1700 may be removably attached to stocking (or garter/body belt) 1706 or socks 1708. However, the feminine needs container 1700 may be attached to any garment that allows the feminine needs container to be substantially concealed from public view, such as pants, skirt, shorts, bathing suit or body belt, and the like.

In some embodiments, the feminine needs container or parts thereof are suitable for repeat usage. In other embodiment, the feminine needs container or parts thereof can be disposable. For example, the feminine needs container can be formed of biodegradable/organic material so that it is environmental friendly and, for example, can be flushed down the toilet, While embodiments and applications of this invention have been shown and described, it would be apparent to those skilled in the art having the benefit of this disclosure that many more modifications than mentioned above are possible without departing from the inventive concepts herein. For example, the closure member may be a drawstring or any other similar closure device.

What is claimed is:

1. A feminine needs container for attachment to an undergarment, the feminine needs container comprising:
    a tubular elongated member having a hollow compartment, a first end, a second end, and a first length;
    a clothing attachment member configured to removably attach to the undergarment and having a second length less than the first length, the clothing attachment member coupled to a side of the elongated member; and
    an outer sheath placed around the elongated member, the outer sheath formed of a soft material to protect the user's skin when the container is removably attached to the undergarment;
    wherein the hollow compartment is configured to receive and store at least one feminine needs product, wherein the elongated member is removably attachable to the undergarment via the clothing attachment member, and wherein the feminine needs container may be concealed from public view while attached to the undergarment.

2. The feminine needs container of claim 1, further comprising:
    a closure member coupled to the first end or the second end of the elongated member to conceal the at least one feminine needs product in the feminine needs container.

3. The feminine needs container of claim 2, wherein the clothing attachment member is coupled to the closure member.

4. The feminine needs container of claim 1, wherein the at least one feminine needs product is a tampon.

5. The feminine needs container of claim 1, wherein the hollow compartment is divided into a plurality of divisions, each of the plurality of divisions extending substantially between the first end and the second end of the elongated member, wherein each of the plurality of divisions are configured to receive and substantially conceal the at least one feminine needs product.

6. The feminine needs container of claim 1, wherein the elongated member is made from a fabric, a plastic, or a combination of fabric or plastic.

7. The feminine needs container of claim 1, wherein the elongated member further comprises an interior liner.

8. The feminine needs container of claim 1, wherein the elongated member further comprises:
    a holding member positioned between the first end and the second end, the holding member designed to secure the at least one feminine needs product within the hollow compartment.

9. The feminine needs container of claim 1, wherein the elongated member further comprises:
    a pressure fit member positioned between the first end and the second end, the pressure fit member designed to secure the at least one feminine needs product within the hollow compartment by exerting pressure on the at least one feminine needs product against the feminine needs container.

10. The feminine needs container of claim 1, wherein the elongated member is made from a malleable and compressible material.

11. The feminine needs container of claim 1, wherein the elongated member further comprises:
    at least one compressible section positioned between the first end and the second end,
    wherein the at least one compressible section is adjustable.

12. The feminine needs container of claim 1, wherein the elongated member is lightweight, waterproof and disposable.

13. The feminine needs container as recited in claim 1, wherein the elongated member is compressible,
    wherein the compressible elongated member configured to receive at least one feminine needs product when the compressible elongated member is expanded between the first end and the second end, and
    wherein the compressible elongated member comprises at least one divider slat configured to be received by the hollow compartment, the at least one divider slat extending from the first end to the second end to divide the hollow compartment into a plurality of sections.

14. The feminine needs container of claim 13, further comprising:
    a closure member coupled to the first end of the compressible member, the second end of the compressible elongated member or along a side of the compressible elongated member to conceal the at least one feminine needs product in the feminine needs container.

15. The feminine needs container of claim 13, wherein the compressible elongated member is tubular.

16. The feminine needs container of claim 13, wherein the at least one feminine needs product is a tampon.

17. The feminine needs container of claim 13, wherein the compressible elongated member is comprised of at least one flexible segment and at least one rigid segment.

18. The feminine needs container of claim 13, wherein each of the plurality of sections extending between the first end and the second end of the compressible elongated member, and each of the plurality of sections configured to receive and conceal the at least one feminine needs product.

19. The feminine needs container of claim 13, wherein the compressible elongated member further comprises an interior liner.

20. The feminine needs container of claim 13, wherein the compressible elongated member further comprises a holding member configured to secure the at least one feminine needs product within the hollow compartment, the holding member positioned between the first end and the second end.

21. The feminine needs container of claim 13, wherein the compressible elongated member further comprises a pressure fit member configured to secure the at least one feminine needs product within the hollow compartment by exerting pressure on the at least one feminine needs product against the feminine needs container, the pressure fit member positioned between the first end and the second end.

22. The feminine needs container of claim 13, wherein the compressible elongated member is of a color to match a skin tone of a user or the color of the garment.

23. A feminine needs container for attachment to an undergarment, the feminine needs container comprising:
- a concealable tubular elongated member having a first end, an uncompressed length, and at least one collapsible region, the concealable elongated member being concealed and undetected from public view when attached to the undergarment;
- the at least one collapsible region configured to compress the concealable elongated member to a compressed position, the compressed position having a compressed length of less than 2 inches;
- a hollow compartment within the concealable elongated member, the hollow compartment configured to receive at least one feminine needs product;
- a clothing attachment member coupled to a side of the concealable elongated member and configured to removably attach to the undergarment, the clothing attachment member having a second length less than the first length when the concealable elongated member is in a uncompressed position;
- an outer sheath placed around the elongated member, the outer sheath formed of a soft material to improve comfort when the feminine needs container is concealed against the user's skin; and
- a closure member coupled to the first end to conceal the at least one feminine needs container within the hollow compartment.

\* \* \* \* \*